United States Patent [19]
Markowitz

[11] Patent Number: 6,120,756
[45] Date of Patent: Sep. 19, 2000

[54] TOPICAL ANIONIC SALICYLATE FOR DISORDERS OF THE SKIN

[75] Inventor: Philip I. Markowitz, 349 Stevens St., Philadelphia, Pa. 19111

[73] Assignee: Philip I. Markowitz, Philadelphia, Pa.

[21] Appl. No.: 09/136,267

[22] Filed: Aug. 19, 1998

[51] Int. Cl.$^7$ .............................. A61K 7/06; A61K 7/00; A61K 7/42; A61K 6/00
[52] U.S. Cl. ...................... 424/70.1; 424/70.11; 424/401; 424/59; 514/887; 514/844; 514/845; 514/846; 514/847
[58] Field of Search ............................. 424/70.1, 70.11, 424/401, 59; 514/887, 844, 845, 846, 847

[56] References Cited

U.S. PATENT DOCUMENTS

| | | | |
|---|---|---|---|
| 3,790,671 | 2/1974 | Sim | 424/230 |
| 4,126,681 | 11/1978 | Reller | 424/181 |
| 4,136,165 | 1/1979 | Möller et al. | 424/60 |
| 4,219,548 | 8/1980 | Reller | 424/234 |
| 4,299,826 | 11/1981 | Luedders | 424/181 |
| 4,440,777 | 4/1984 | Zupan | 424/274 |
| 4,514,385 | 4/1985 | Damani et al. | |
| 4,665,063 | 5/1987 | Bar-Shalom | 514/164 |
| 4,671,956 | 6/1987 | Bouillon et al. | 424/59 |
| 4,891,227 | 1/1990 | Thaman | 424/443 |
| 4,933,330 | 6/1990 | Jorgensen et al. | 514/159 |
| 5,019,567 | 5/1991 | Phillippe et al. | 514/164 |
| 5,262,407 | 11/1993 | Leveque et al. | 514/159 |
| 5,559,098 | 9/1996 | Wohlrab et al. | 514/29 |
| 5,616,572 | 4/1997 | Blank | 514/159 |
| 5,652,266 | 7/1997 | Bobier-Rival et al. | 814/557 |
| 5,723,109 | 3/1998 | Causse et al. | 424/62 |
| 5,728,732 | 3/1998 | Corey et al. | 514/544 |
| 5,741,497 | 4/1998 | Guerrero et al. | 424/401 |
| 5,773,015 | 6/1998 | Bajor et al. | 424/401 |

OTHER PUBLICATIONS

File registry, salicylate structure and comparative names, ACS,RN 63–36–5.

Olin et al., Facts and Comparisons, St. Louis, MO: JB Lippincott, p. 62, Apr. 1986.

Lehninger, A.L., *Biochemistry*, Worth Publishers, Inc., New York, NY, p. 584 (1982).

Williams, M.L. et al., "Exogenous origins of n–alkanes in pathologic scale", *Archives of Dermatology*, 128(8):1065–71 (1992).

*Cinical Toxicology of Commercial Products*, Gosselin, R.E., Smith, R.P., Hodge, H.C., Williams & Wilkins, Baltimore, MD, p. II–177 (1984).

Reed, G.A., Ryan, M.J., "Peroxyl radical–dependent epoxidation of cyclopenteno[ac,d]pyrene", *Carcinogenesis*, 11(10):1825–9 (1990) (Abstract Only).

Wistuba, D. et al., "Cytochrome P–450 catalyzed asymmetric epoxidation of simple prochiral and chiral aliphatic alkenes: species dependence and effect of enzyme induction on enantioselective oxirane formation", *Chirality*, 1(2):127–36 (1989) (Abstract Only).

Verschueren, K., *Handbook of Environmental Data on Organic Chemicals*, Van Nostrand, pp. 36, 48, 900 and 1484 (1996).

Lin, J.K., "Nitrosamines as potential environmental carcinogens in man", *Clinical biochemistry*, 23(1):67–71 (1990) (Abstract Only).

Farivar, R.S., Brecher, P., Salicylate is a transcriptional inhibitor of the inducible nitric oxide synthase in cultured cardiac fibroblasts, *Journal of Biological Chemistry*, 271(49):31585–31592 (1996).

Schwenger, P. et al., "Sodium salicylate induces apoptosis via p38 mitogen–activated protein kinase but inhibits tumor necrosis factor–induced c–Jun N–terminal kinase/stress–activated protein kinase activation", *Proc. Natl. Acad. Sci. USA*, 94:2869–73 (1997).

Elder et al., "Differential growth inhibition by the aspirin metabolite salicylate in human colorectal tumor cell lines: enhanced apoptosis in carcinoma and in vitro–transformed adenoma relative to adenoma cell lines", *Cancer Research*, 56:2273–6 (1996).

Khan, K.A., "Comparative genotoxicity of six salicylic acid derivatives in bone marrow cells of mice", *Mutation Research*, 370(1):1–9 (1996).

Goodman and Gilman, "The Pharmacological Basis of Therapeutics", Hardman, J.G. and Limbird, L.E. (Eds), *Analgesic–Antipyretic and Antiinflammatory Agents*, McGraw–Hill, New York, NY, p. 628 (1996).

Williams, M.L., Elias, P.M., "Elevated n–alkanes in congenital ichthyosiform erthroderma. Phenotypic differentiation of two types of autosomal recessive ichthyosis", *Journal of Clinical Investigation*, 74(1):296–300 (1984).

Brown, B.E. et al., "Stratum corneum lipid abnormalities in ichthyosis. Detection by a new lipid microanalytical method", *Archives of Dermatology*, 120(2):204–9 (1984).

Sagone, A.L., Husney, R.M., "Oxidation of salicylates by stimulated granulocytes:evidence that these drugs act as free radical scavengers in biological systems", *Journal of Immunology*, 138(7):2177–83 (1987).

Maskos, et al., "The hydroxylation of the salicylate anion (italics added) by a Fenton reaction and T–radiolysis: a consideration of the respective mechanisms", *Free Radical Biology and Medicine*, 8(2):153–62 (1990).

(List continued on next page.)

*Primary Examiner*—Johann Richter
*Assistant Examiner*—Diedra Faulkner

[57] ABSTRACT

A method of treating or preventing a skin disorder caused by at least one of excessive sebum production and abnormal keratinocyte proliferation, the method comprising topically administering to a region of the skin of a human affected by or susceptible to a skin disorder caused by at least one of excessive sebum and abnormal keratinocyte proliferation, a composition comprising anionic salicylate in an amount effective to reduce or stop the occurrence or delay the occurrence of at least one of the excessive sebum production and abnormal keratinocyte proliferation.

19 Claims, 5 Drawing Sheets

OTHER PUBLICATIONS

Fischer–Nielsen, A., et al., "Radiation–induced formation of 8–hydroxy–2–deoxyguanosine and its prevention by scavengers", *Carcinogenesis*, 15(8):1609–12 (1994) (Abstract Only).

Dong, Z., "Inhibition of ultraviolet B–induced activator protein–1 (AP–1) activity by aspirin in AP–2–luciferase transgenic mice", *Journal of Biological Chemistry*, 272(42):26325–31 (1997).

Peter M. Elias et al., "Lipids and the Epidermal Water Barrier: Metabolism, Regulation, and Pathophysiology," *Seminars in Dermatology*, 11(2):176–182 (Jun. 1992).

Mary L. Williams, "Epidermal Lipids and Saling Diseases of the Skin," *Seminars in Dermatology*, 11(2):169–175 (Jun. 1992).

Gerald Weissmann, "Aspirin," *Scientific American*, pp. 84–90 (Jan. 1991).

Product Info. Sheet of Very Europe S.P.A., Genova, Italy, "BTN®," 7 pages (1991).

"Tridecanol (mixtures of isomers)," Chemical Safety Sheets, Kluwer Academic Publishers, Dordrecht, Netherlands, p. 882 (1991).

Single Sheet re. 1–dodecanol, *Handbook of Environmental Data on Organic Chemicals*, Verschueren, Van Nostrand Reinhold, New York, NY (1996).

Single Sheet re. 1–octanol, *Handbook of Environmental Data on Organic Chemicals*, Verschueren, Van Nostrand Reinhold, New York, NY (1996).

P.E. Kolattukudy, "Biosynthesis of Surface Lipids," *Science*, 159:498–505 (1968).

Paige E. Tolbert, "Oils and cancer," *Cancer Causes and Control*, 8:386–405 (1997).

English Abstract Only13 J.K. Lin, "Nitrosamines as potential environmental carcinogens in man," Source: *Clinical Biochemistry*, 23(1):67–71 (Feb. 1990).

*The Merck Index*, Eleventh Edition, publ. Merck & Co., Inc., Rahway, NJ, pp. 1367–1368, p. 893 (1989).

Ernst Zander, M.D., et al., "Treatment of Acne Vulgaris with Salicylic Acid Pads," *Clinical therapeutics*, 142(2):247–253 (1992).

Peter Goldman, "The Inhibition of the Biosynthesis of Long–Chain Fatty Acids by Salicylate and Nicotinate," *Biochemical Pharmacology*, 16:47–52 (1967).

A.N. Klimov et al., "The effect of salicylate on the activity of a cetyl–CoA carboxylase in rat liver," *Biochemical Pharmacology*, 26:898–899 Pergamon Press, Printed in Great Britain (1979).

Usha Dular et al., "Effect of Salicylates on Acetyl Coenzyme A Carboxylase," *Biochemical Pharmacology*, 28:715–718, Pergamon Press Ltd., Printed in Great Britain (1979).

M.J.H. Smith et al., "Salicylate and enzymes," *J. Pharm. Pharmac.*, 23:729–744 (1971).

P.D. Dawkins et al., "The mechanism of the inhibition of dehydrogenases by salicylate," *J. Pharm. Pharmac.*, 19:355–366 (1967).

James J. Leyden, M.D., "Review Article—Drug Therapy—Therapy for Acne Vulgaris," *The New England Journal of Medicine*, Alastair J.J. Wood, M.D., Ed., pp. 1156–1162 (Apr. 17, 1997).

TOPICAL ANIONIC SALICYLATE FOR DISORDERS OF THE SKIN

FIELD OF THE INVENTION

The present invention relates to treatment and prevention of skin disorders caused by excessive production of sebum, or abnormal proliferation of keratinocytes, or both.

BACKGROUND OF THE INVENTION

There are many skin disorders associated with the excessive production of sebum, or the abnormal proliferation of keratinocytes, or both. Examples of skin disorders include acne vulgaris, seborrheic dermatitis (also referred to as seborrheic eczema), seborrheic adiposa (also referred to as seborrheic oleosa), seborrheic sicca, psoriasis, eczema, contact dermatitis, irritant dermatitis, ichthyosis and keratosis pilaris. Seborrheic dermatitis is characterized by moderate erythema, dry, moist, or greasy scaling, and yellow crusted patches on various skin areas of the body, including the mid-parts of the face, ears, supraorbital regions, umbilicus, genitalia, and especially the scalp. Seborrheic adiposa is described as oily secretion occurring especially about the nose and forehead. Seborrheic sicca is characterized as dry scaly seborrheic dermatitis. Psoriasis is characterized by scaly, erythematous plaques that may become confluent. Ichthyosis is a non-inflammatory scaling, hyperkeratotic disorder of skin. Keratosis pilaris, or multiple keratin plugs in skin follicles, produces a bumpy appearance to the skin. Hyperkeratosis is common in chronic contact, irritant and atopic (eczema) dermatitis.

Acne vulgaris, more commonly called acne, is a common skin disorder affecting a large number of people. Acne can result in physical damage such as scarring or disfigurement. Additionally, acne can cause adverse emotional effects to the individuals afflicted with the condition. Acne results when sebaceous follicles, located primarily on the face and trunk, become obstructed with sebum and epithelial cells. Sebum is produced by sebaceous glands in the follicles and epithelial cells are desquamated from the walls of the follicles. The sebum and the desquamated epithelial cells obstruct the sebaceous follicles. Obstruction of the follicles creates microcomedones which may evolve into comedones (non-inflammatory lesions, e.g., open and closed comedones, i.e., whiteheads and blackheads) or inflammatory lesions (e.g., inflammatory nodules, pustules and papules). A residing anaerobic bacterium, *Propionibacterium acnes* (*P. acnes*) proliferates in this environment of excessive sebum and follicular cells and may produce localized inflammation. Acne can be primary (idiopathic) or secondary (due, for example, to the application of cosmetics). Included in the definition of acne for the purposes of the present invention are cosmetically undesirable skin conditions commonly referred to as pimples, blemishes, skin imperfections, etc.

Acne is currently treated either topically or systemically (Leyden, 1997, *New Engl. J. Med.* 336(16):1156–1162). Treatment of acne involves controlling sebum production, reducing epithelial cell proliferation, or both. The primary etiologic factor in acne is now thought to be excessive sebum production. A treatment best able to modify this will be most efficacious. The present state of the art is such that treatment with systemic drugs is the only current way to control excessive sebum production. These drugs are prescribed as therapies only in severe cases of acne. Drugs known to be effective in controlling sebum overproduction include estrogens, antiandrogens such as cyproterone acetate, spironolactone, and the retinoid isotretinoin.

Estrogen treatments for reducing sebum production are usually prescribed as a combination estrogen-progestin contraceptive. A high dose of estrogen is maximally beneficial, increasing the well-known risks of oral contraceptive therapy. A therapeutic response is slow in onset, not appearing for two to four months. Prolonged treatment is necessary. There are also disadvantages to the use of spironolactone to reduce sebum production. Maximal benefits of spironolactone are also delayed, and continual treatment with the drug is necessary to maintain the improvement. Therapeutic results are only modest because spironolactone is only a weak anti-androgen.

Because sebaceous glands are androgen-dependent, systemic administration of anti-androgens, such as cyproterone acetate, is an effective treatment. However, the use of anti-androgens is limited to nonpregnant women because of potential feminizing effects on a male fetus and demasculinizing effects in adult males.

In severe recalcitrant cases of acne, oral administration of isotretinoin is effective in reducing sebum production, but the use of this compound is limited by cost, adverse side effects and teratogenicity.

Antibiotics, both systemic and topical, are used to decrease the proliferation of *P. acnes*, the bacterium responsible for the inflammatory lesions of acne. Systemic antibiotic treatments include tetracycline, erythromycin, minocycline, doxycycline, clindamycin, and trimethoprim-sulfamethoxazole. Topical antibiotic therapy for acne may include the administration of erythromycin, clindamycin, sulfacetamide, azelaic acid, benzoyl peroxide, or a combination of benzoyl peroxide and either erythromycin or glycolic acid. Although *P. acnes* is sensitive to many antibiotics in vitro, delivery of the antibiotics to the lipid-rich environment of the sebaceous follicles, in which the organism resides and proliferates, is difficult. Erythromycin is poorly lipophilic, clindamycin somewhat more so. Their efficacy is comparable. Benzoyl peroxide, although more lipophilic, also has its limitations. Although benzoyl peroxide is more effective in suppressing the growth of *P. acnes* than the topical formulations of clindamycin and erythromycin, benzoyl peroxide does not have any antinflammatory properties. Moreover, another disadvantage to using benzoyl peroxide in acne treatment is the local irritation and allergic contact dermatitis that may occur in the area of the skin being treated. Animal studies suggest that it may be carcinogenic. The disadvantage of using antibiotics as a treatment of acne is that most individuals require prolonged or frequent intermittent courses of antibiotic administration. Additionally, *P. acnes* is beginning to develop some antibiotic resistance, calling into question the future efficacy of antimicrobial therapy. It also contributes to the generalized development of antibiotic resistance in other pathogenic bacteria. Serious drug reactions have been associated with the use of clindamycin and sulfa drugs.

There has been little therapeutic progress since the introduction of retinoic acid and benzoyl peroxide two decades ago. Azelaic acid, just recently introduced, is not superior to any other topical therapies. Oral isotretinoin is highly effective but not widely available or applicable due to its significantly adverse side effect profile. The strict requirement for contraception is difficult to enforce, particularly in adolescents. There is clearly a need for an effective, safe and cosmetically palatable topical acne treatment.

The prior art describes no topical therapy for decreasing sebum production. Currently, excessive production of sebum is typically treated with facial cleansers, like soaps, detergents, and astringents, that work by merely removing sebum from the surface of the skin, rather than by reducing or inhibiting sebum production. The use of facial cleaners is actually counterproductive for a number of reasons. Cleansers and astringents emulsify necessary epidermal lipids and overly dry the skin. They paradoxically increase sebum production by causing hyperplasia of sebaceous glands and an increase in the cellular organelles responsible for sebum synthesis in sebocytes. Facial oiliness can be masked by "oil free" cosmetic preparations that contain clays, talcs, silicas, starches, polymers and other materials that temporarily absorb oil like a sponge. These formulations are limited by their sebum-absorbing capacity, formulation difficulties, negative aesthetic properties, and limited duration of effect. Women with acne may attempt to camouflage the symptoms by excessive application of makeup. Makeup is comedogenic and produces additional acne lesions.

Excessive follicular epithelial proliferation, keratinization and desquamation in sebaceous follicles leads to the formation of microcomedones. Known topical therapies for modifying the desquamation of follicular epithelial cells include the administration of retinoids such as tretinoin, isotretinoin and tazarotene, and the desquamating agent salicylic acid. Abnormal proliferation of keratinocytes produces follicular plugging, allowing sebum stasis and bacterial overgrowth. This results in increased bacterial hydrolysis of triglycerides to irritating free fatty acids and the inflammatory papulopustular lesions characteristic of acne.

Salicylic acid, therapeutically classified as a keratolytic agent, is extensively used as a desquamating agent. Salicylic acid exfoliates skin and leads to the extrusion of comedones, the primary lesion of acne. Unfortunately, salicylic acid is irritating and is limited to concentrations that are only partially efficacious. Salicylic acid has no effect on the production of sebum. Salicylic acid is not the preferred topical treatment; rather, benzoyl peroxide is more commonly used, suggesting that salicylic acid has only modest efficacy in the treatment of acne. In acne preparations, salicylic acid is used in concentrations of 0.5% to 2.0%. At a concentration of 0.5%, this compound is probably ineffective, at best minimally effective; however, the 0.5% concentration is marketed for the treatment of acne in individuals with sensitive skin. Salicylic acid at a concentration of 2.0% has modest efficacy. Efficacy potentially could be enhanced by increasing the concentration, however, such increased concentrations are contraindicated, since salicylic acid is extremely irritating because of its high acidity with a pH of 2.4. At a concentration of 17%, salicylic acid is commercially available to treat verruca vulgaris (warts) but carries a warning that this compound should not be applied to normal skin surrounding the lesion; irritated, infected or reddened skin; moles, birthmarks or hairy warts; or the face or mucuos membranes. Diabetics or individuals with circulatory problems are advised not to use it due to the risk of severe ulceration (*Physicians' Desk Reference*, Medical Economics Company, Montvale, N.J., p. 982 (1998). Salicyclic acid at a concentration of 5% is marketed to peel callouses and excessively cornified skin. It would not be appropriate for the tender and less cornified skin of the face. The prior art discloses methods to decrease its irritant properties by combination with pantothenic acid (U.S. Pat. No. 5,612,324) and ascorbic acid (U.S. Pat. No. 5,516,793). Its use in acne is reserved for mild cases primarily involving comedones and papules without a significant pustular or nodular component. This is also the case for benzoyl peroxide. Antibiotics and retinoic acid derivatives are more likely to be used in severe cases. The present invention further departs from the prior art by its applicability and therapeutic efficacy across the spectrum of disease severity.

Topical application of retinoic acid also decreases comedone formation. This compound may decrease follicular epithelial cell adhesion and may beneficially modulate cellular proliferation. Unfortunately, retinoic acid is very drying and irritating to the applied area. Furthermore, retinoic acid results in an increase in photosensitivity, making it necessary for the user to diligently avoid sun exposure.

The prior art describes the topical administration of derivatives of salicylic acid. U.S. Pat. No. 4,126,681 discloses compositions and methods for topical administration of an anti-inflammatory amount of acetylsalicylic acid to inflamed tissue. U.S. Pat. No. 4,665,063 discloses a composition and a method for the treatment of dermatological disorders by topically applying acetylsalicylic acid within a carrier. U.S. Pat. No. 4,933,330 discloses a composition and method for use in the treatment of psoriasis comprising 4-aminosalicylic acid or 5-aminosalicylic acid. The prior art employs these agents because they are anti-inflammatory; they do not address any of the other etiologic factors in acne. Incorporation of salicylate compounds into acne preparations has been suggested in order to improve the activity of the therapeutic ingredient. U.S. Pat. No. 5,019,567 discloses the use of quaternary ammonim lipophilic salicylate compounds to increase the stability of benzoyl peroxide and retard its decomposition. U.S. Pat. No. 4,299,826 discloses the use of a variety of penetration-enhancing agents for topical erythromycin compositions including benzyl and ethyl salicylate. U.S. Pat. No. 5,559,098 discloses the use of alkyl salicylate compounds to increase the lipophilicity of erythromycin in topical formulations.

Additionally, these compounds have drawbacks. Allergic reactions to acetylsalicylic acid are common, particularly in individuals with asthma, eczema and other allergic conditions. A disadvantage to using either 5-aminosalicylic acid or 4-aminosalicylic acid is that these compounds are chemically unstable on exposure to air and light, which results in shortened shelf life of the product. Furthermore, the *U.S. Pharmacopia National Formulary*, United States Pharmacopeial Convention, Inc., Rockville, Md., pp. 89–92 (1994) explicitly states that a prepared solution of 5-aminosalicylic acid or 4-aminosalicylic acid should not be used after 24 hours following preparation or if the product becomes discolored. Both are decarboxylated to the light-sensitive dye m-aminophenol. Since these compounds become easily discolored upon exposure to air and light, staining can occur of objects (e.g., clothes, linens, vanities) that contact either the compound or skin that has been treated with the compound. This is clearly pharmaceutically and cosmetically unacceptable. Moreover, it appears that the metabolism of 5-aminosalicylic acid to anionic salicylate does not occur in vivo; therefore, 5-aminosalicylic acid is not considered a true salicylate. (G. K. McEvoy, Ed., *AHFS Drug Information*, Section 56:40, p. 2434, American Society of Hospital Pharmacists, Inc., Bethesda, Md. (1998).)

There is a need for a method for treating and preventing excessive sebum production and abnormal keratinocyte proliferation with a topical agent, which is not keratolytic and caustic (thereby inhibiting the sebum production and abnormal keratinocyte proliferation) to inhibit skin disorders associated with these conditions. The present invention satisfies this need and overcomes the deficiencies of prior art treatments.

Salicylate salts and derivatives are extensively used in the oral form for the treatment of fever, pain and inflammation.

This is based on their ability at therapeutic doses to inhibit prostaglandin synthesis. The prior art recognizes the use of topical salicylate containing compounds only as sunscreens (e.g., octyl salicylate) and anti-rheumatic agents (e.g., methyl salicylate).

The present invention is based on the discovery that anionic salicylate has the ability to prevent and treat acne and other skin disorders associated with the production of excessive sebum or abnormal proliferation of keratinocytes, without adversely affecting the skin at the dosage level necessary to reduce excessive sebum production or abnormal keratinocyte proliferation. The treatment may be prophylactic, palliative or curative.

SUMMARY OF THE INVENTION

One aspect of the invention relates to a method of treating a skin disorder caused by at least one of excessive sebum production and abnormal keratinocyte proliferation, the method comprising topically administering to a region of the skin of a human having a skin disorder caused by at least one of excessive sebum production and abnormal keratinocyte proliferation, a composition comprising anionic salicylate in an amount effective to reduce at least one of excessive sebum production and abnormal keratinocyte proliferation.

Another aspect of the invention relates to a method of preventing a skin disorder caused by at least one of excessive sebum production and abnormal keratinocyte proliferation, the method comprising topically administering to a region of the skin of a human susceptible to a skin disorder caused by at least one of excessive sebum production and abnormal keratinocyte proliferation, a composition comprising anionic salicylate in an amount effective to stop the occurrence or delay the occurrence of at least one of the excessive sebum production and abnormal keratinocyte proliferation.

The disclosures of all publications and patents referred to herein are hereby incorporated herein by reference.

DETAILED DESCRIPTION OF THE INVENTION

Definitions

Figure 1:
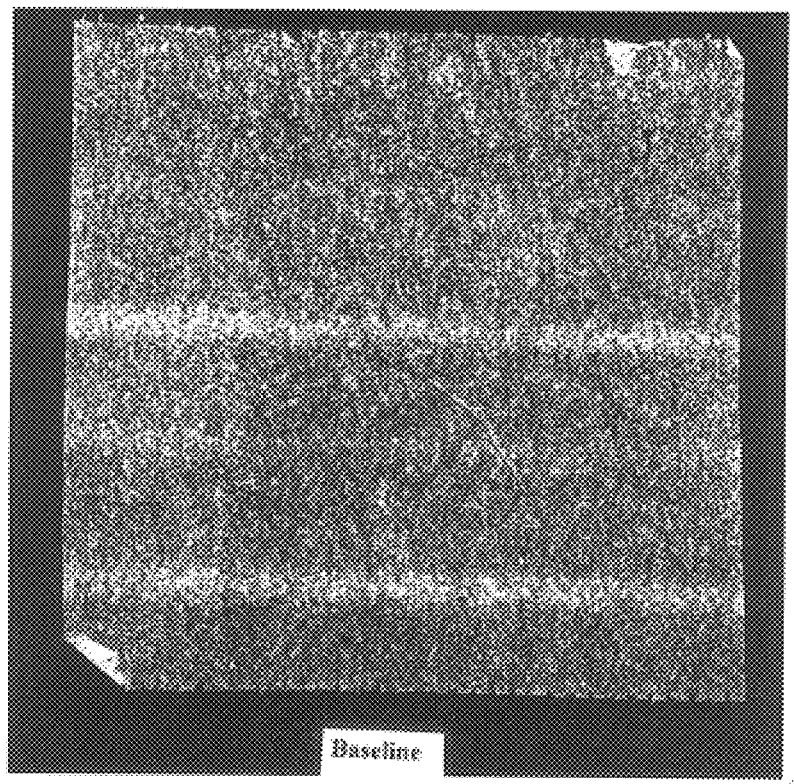
FIG. 1 is a photograph of a tissue paper blot of an individual's forehead immediately after cleansing with soap and water and drying, to establish a baseline for sebum production.

"Abnormal proliferation of keratinocytes" or the equivalent term "abnormal keratinocyte proliferation" as used herein means either the production of excessive keratinocytes or the abnormal differentiation of epidermal cells to keratinocytes, or both, which results in a skin disorder.

"Keratolytic" as used herein is defined as referring to an agent which results in the peeling or removal of the cornified layer of the epidermis.

"Percent" or "%" as used herein is defined in respect to components or ingredients of a compound, composition or mixture as the weight percentage of the component or ingredient based on the weight of the compound, composition or mixture containing it, unless otherwise indicated.

"Preventing" as used herein is defined as stopping the occurrence or delaying the occurrence of a skin disorder.

"Seborrheic dermatitis" as used herein is defined as chronic inflammatory disease of the skin associated with excessive sebum production.

"Treatment" as used herein is defined as eliminating, alleviating, or relieving symptoms of a skin disorder.

Description

The present invention is a method for treating or preventing a skin disorder caused by at least one of excessive sebum production and abnormal keratinocyte proliferation, the method comprising topically administering to a region of the skin of a human affected by a skin disorder or susceptible to a skin disorder caused by at least one of excessive sebum production and abnormal keratinocyte proliferation, a composition comprising anionic salicylate in an amount effective to reduce or stop the occurrence or delay the occurrence of at least one of the excessive sebum production and abnormal keratinocyte proliferation. Skin disorders treated in this invention include those associated with excessive sebum production or abnormal proliferation of keratinocytes, skin cells that synthesize keratin. Such skin disorders include, without limitation, acne, seborrhea, seborrheic dermatitis or seborrheic eczema, seborrheic adiposa or seborrheic oleosa, seborrheic sicca, keratosis pilaris, psoriasis, eczema, contact dermatitis, irritant dermatitis and ichthyosis.

The present invention is based on the discovery that anionic salicylate has the ability to prevent and treat acne and other skin disorders associated with the production of excessive sebum or abnormal proliferation of keratinocytes, without adversely affecting the skin at the dosage level necessary to reduce excessive sebum production or abnormal keratinocyte proliferation.

Anionic salicylate suppresses sebum production and keratinocyte proliferation. To the contrary, salicylic acid cannot for a number of reasons. Concentrations of salicylic acid sufficient to reduce sebum production and keratinocyte proliferation cannot be used without causing adverse effects, such as severe irritation and inflammation, to the treated area.

Pharmacologically, salicylic acid is a prodrug for anionic salicylate, since it must be converted to the ionic form in order to be metabolically active. This readily occurs in an aqueous, mildly alkaline environment such as that present in most cells. It does not occur to any significant degree in the skin due to the skin's mildly acid pH, the non-aqueous environment of the lipid-rich sebaceous glands and intercellular matrix that surrounds keratinocytes (the primary diffusion paths for the ingress of topically active agents), and salicylic acid's rapid transit time through the epithelial barrier. Salicylic acid's relatively high octanol/water partition coefficient favors partititon into the lipid rather than the aqueous compartment of skin. Topically applied salicylic acid remains a neutral solute. Therefore, for the purposes of the present invention, therapeutic efficacy requires the direct topical application of salicylate in an ionic or salt state. Anionic salicylate can be applied to the skin in extraordinarily high concentrations due to its neutral pH. This facilitates lipophilicity due to the high concentration gradient that can be attained.

The precise mechanism by which anionic salicylate is effective is not known. However, without wishing to be bound by any particular theory, the inventor believes that anionic salicylate is effective based on the following mechanisms. The pathogenesis of acne is multifactorial. Anionic salicylate possesses numerous biological properties, a number of which are relevant to the pathogenesis of acne. Anionic salicylate inhibits sebum production through two mechanisms. First, this compound inhibits lipid synthesis by inhibiting the rate limiting enzyme involved in fatty acid synthesis, acetyl CoA carboxylase. Since sebum is composed of triglycerides, free fatty acids and cholesterol, and fatty acids are the building blocks of triglycerides, preventing lipid synthesis will inhibit sebum production. Second, anionic salicylate inhibits the NADPH-dependent enzyme 5-α-reductase, which converts testosterone into its more potent metabolite, dihydrotestosterone. Dihydrotestosterone potently stimulates sebum production and sebaceous gland hypertrophy. Since the conversion to this active form of testosterone has been demonstrated to be markedly increased in individuals with acne, the inhibition of dihydrotestosterone production results in the reduction of sebum production, thereby preventing the occurrence of acne. Anionic salicylate antagonizes the epidermal growth factor receptor, as well as enzymes and transcription factors involved in DNA and RNA synthesis. This beneficially modulates cellular proliferation. By interfering with energy metabolism, it is bacteriostatic. Moreover, since anionic salicylate is a potent anti-inflammatory agent this compound ameliorates the inflammatory lesions that are characteristic of acne. Finally, anionic salicylate inhibits stress induced, catecholamine modulated lipolysis of triglycerides to irritant-free fatty acids, the reason that skin breaks out under stress.

Anionic salicylate retards comedone formation by preventing the hyperproliferation of skin cells responsible for follicular occlusion. The prior art does not recognize salicylate as being antiproliferative. Inhibition of epidermal cell growth is demonstrated by decreased comedone formation in individuals with acne. Inhibition of cellular proliferation leads to the amelioration of acne and other skin disorders characterized by abnormal proliferation of keratinocytes or fibroblasts.

The present invention exploits another biological property of anionic salicylate that makes the use of anionic salicylate a novel treatment of acne. Anionic salicylate is bacteriostatic due to its ability as noted above to uncouple oxidative phosphorylation and block bacterial energy metabolism. These bacteriostatic effects are anti-bacterial against *P. acnes*, the bacterium responsible for acne lesions. The inhibitory effect on *P. acnes* is dependent on achieving sufficiently high concentrations in the sebaceous glands where *P. acnes* resides. Topical antibiotic therapy is limited in this regard. Topical anionic salicylate overcomes this deficiency in the prior art.

The present invention is unique in that this invention exploits biologic effects of anionic salicylate that in one context, as a systemic treatment, would be toxic, but in the context of the present invention, as a topical treatment, are therapeutic, thereby going well beyond the deficiencies of the prior art treatments. The prior art does not recognize salicylate as possessing anti-seborrheic, antiproliferative and antibacterial properties. The present invention comprising the topical administration of anionic salicylate is the only single topical treatment that addresses the inflammatory, proliferative and seborrheic aspects of the skin disorders discussed above, including all of the etiologic factors in acne.

The composition of the anionic salicylate according to the present invention for treating and preventing a skin disorder may comprise at least about 0.5%, preferably about 5% to about 75%, more preferably about 10% to about 50%, and most preferably about 10% to about 20% of anionic salicylate. The concentration chosen for the anionic salicylate is based upon the condition and individual being treated and the empirical results noted for the condition and individual. It is generally desired to use the minimum effective amount, although adverse effects have not been observed for anionic salicylate even at 50% concentrations presently desired to treat seborrhea. For acne treatment, a concentration of anionic salicylate of about 10% to about 20% is presently preferred. Certain conditions may be most effectively treated even at very high concentrations, such as about 75%, of anionic salicylate.

Anionic salicylate is the dissociated product of salicylic acid, salicylsalicylic acid or a salicylate salt, namely, a salt of 2-hydroxybenzoic acid or salicylsalicylic acid, where the salicylate salt dissociates into its respective cation and anionic salicylate in aqueous solution. Anionic salicylate can also be produced by dissolving salicylsalicylic acid or salicylic acid in an alkaline aqueous medium. Preferred salicylate salts for use in the present invention include sodium salicylate, magnesium salicylate, choline salicylate, and choline magnesium trisalicylate. Salicylate salts are known compounds and are available commercially from a variety of sources.

A preferred concentration of anionic salicylate employed herein is prepared by dissolving 10 grams (g) of a salicylate salt, such as sodium salicylate, choline magnesium trisalicylate, choline salicylate, or magnesium salicylate, in enough distilled water to yield 100 g of solution (a 10% solution) of anionic salicylate. Likewise, a 20% composition of anionic salicylate, another preferred concentration, is prepared by dissolving 20 g of salicylsalicylic acid in an alkaline medium, e.g, carbonated water sufficient to yield 100 g of solution. The dissociated product, referred to herein as anionic salicylate foundation, need not be separated from and includes the respective cation of the starting material, such as magnesium from magnesium salicylate. The anionic salicylate is then mixed with the vehicle of choice depending on the particular composition desired, such as a solution, lotion or gel, cream, etc.

Suitable functional derivatives of anionic salicylate that would be pharmaceutically effective to treat the skin disorders upon topical administration are also included in the present invention. Such derivatives include but are not limited to substitutions yielding salts, esters or amides or modifications of the hydroxy or carboxyl groups, such as substitutions with alkyl, aryl, alkenyl, aminoalkyl, aminoaryl, alkoxy, heteroaryl, nitro, sulpho or halogen groups.

The form of composition of the invention suitable for topical administration may be a cream, ointment, lotion, liniment, gel, solution, suspension, facial wash, paste, stick, spray, shampoo, soap, hair conditioner or powder. It may be incorporated into make-up and other cosmetics. These forms and appropriate ingredients and vehicles can be readily determined in view of this disclosure by one of ordinary skill in making pharmaceutical or cosmetic formulations. See, for example, Genaro, Ed. 1985, *Remington's Pharmaceutical Sciences*, Mack Publishing Co., Easton, Pa., for a variety of forms of topical pharmaceutical compositions that may be adapted readily to the present invention in view of this disclosure.

The pharmaceutical compositions according to the invention may comprise any suitable pharmaceutical, cosmetic or inert excipients or carriers, as well as emulsifying agents, antioxidants, buffering agents, preservatives, humectants, penetration enhancers, coloring agents, chelating agents, gel forming agents, ointment bases, pH-regulators, perfumes and skin protective agents.

Examples of suitable antioxidants which may be used in the compositions according to the invention are: butylated hydroxy anisole (BHA), butylated hydroxytoluene (BHT), ascorbic acid, sodium ascorbate, ascorbyl palmitate, nordihydroguaiaretic acid, propyl gallate, tocopherol and derivatives thereof, hydroquinones, gallic acid, sodium or potassium pyrosulphite, cysteine and cysteine derivatives.

Typical exemplary chelating agents include sodium EDTA, citric acid and phosphoric acid.

Typical exemplary gel forming agents include Carbopol® (B.F. Goodrich Co., New York, N.Y.), cellulose gum, bentonite, alginate, gelatin, polyvinylpyrrolidine (PVP), aluminum hydroxide, or Veegum® (R.T. Vanderbilt Co., New York, N.Y.).

Typical penetration enhancers include ethyl alcohol, isopropyl alcohol, propylene glycol, triethanolamine and surfactants.

Exemplary humectants include glycerin, propylene glycol, sorbitol, mannitol, urea, sodium chloride, lactic acid and xylitol.

Suitable exemplary ointment bases include beeswax, paraffin, cetyl palmitate, vegetable oil, Tween® (ICI United States, Wilmington, Del.) and Span® (ICI United States).

For topical application a pH of about 5 to about 8 is preferred. A more preferred pH is about 7.0 to about 7.5. Conventional buffering agents may be used to obtain the desired pH.

Typical exemplary preservatives include the parabens, formaldehyde, Kathon® CG (Rohm and Haas, Philadelphia, Pa.), Bronidox® (Henkel Komm. A.G., Dusseldorf, Germany), Bronopol® (The Boots Co., Ltd., Nottingham, England), p-chloro-m-cresol, chlorhexidine, benzalkonium chloride, etc.

Conventional ingredients may be used where the compositions of the invention are in the form of a shampoo or a soap, and typical soap and shampoo bases include such exemplary components as tetaine, sodium lauryl sulfate, nonyhlphenol, imidazole, sulphosuccinate, refattening agents, humectants and conditioners.

Typical exemplary solubilizers include ethyl alcohol, glycerin, isopropyl myristate, sorbitol, surfactants and oils.

Suitable exemplary suspending agents include bentonite, gelling agents, kaolin, magnesium hydroxide, agar, magnesium silicate and acacia.

Thus, variable factors in the compositions of the invention may be additives, antioxidants, chelating agents, conditioners, derivatives of the active substances, emulsifying systems, fatty-phases, gel forming agents, humectants, mass ratios, ointment bases, particle sizes, paste bases, penetration enhancers, pH, powder bases, preservatives, propellants, refattening agents, shampoo bases, solubilizers, stick bases, and suspending agents.

Other forms of anionic salicylate are also included, such as semisolid and liquid formulations. Such compositions may be formulated according to conventional pharmaceutical practices. Semisolid formulations may include gels, creams, pastes, and mixtures. Liquid formulations may include solutions, suspensions, lotions, drenches, and emulsions. Micronization of the particles is highly desirable. In some situations, liposomal delivery systems may also be preferred.

The topical administration of a composition of anionic salicylate may be an administration onto or close to the parts of the body presenting the skin disorder caused by at least one of excessive sebum production and abnormal keratinocyte proliferation, e.g., onto an exterior part of the body such as a skin surface. The application may be done simply by applying the composition onto the skin, or it may involve any device suited for enhancing the establishment of contact between the composition and the region of the skin of a human caused by at least one of excessive sebum production and abnormal keratinocyte proliferation. The composition may be impregnated or distributed onto pads, plasters, strips, gauze, sponge materials, cotton wool pieces, etc.

When the composition of anionic salicylate of the present invention is used in the treatment of a skin disorder, the amount of composition topically administered and treatment regimen will vary, depending upon the severity of the state of the skin disorder. Treatment regimes which are contemplated include a dose or dosage which is administered hourly, daily, or at any other intervals which may apply in a given case. Conventionally the composition may be applied 1 to 10 times a day, depending on the type, the severity and the localization of the skin disorder. More frequent applications would be indicated for spot resolution of active lesions, such as pustules or nodules.

When the composition of anionic salicylate is used in the topical treatment of a skin disorder, the preferred treatment will involve applying a safe and effective amount of the composition to a region of the skin of a human caused by at least one of excessive sebum production and abnormal keratinocyte proliferation. The effective dosage is about 2 to about 4 applications of the composition per day. It may be preferable to cleanse the skin prior to the treatment, and any soap or detergent composition suitable for washing the skin can be employed.

When the composition of the present invention is used in a method of preventing a skin disorder, the composition of anionic salicylate is topically administered to a region of the skin of a human that is susceptible to a skin disorder, displaying such symptoms as oily skin, excessive shine to the skin, blemishes, visible comedones. An effective dosage is about 1 to about 3 applications of the composition per day. The composition may be applied to completely normal appearing skin as well, in order to maintain this state.

The invention will be further described by reference to the following detailed Examples. These Examples are provided for purposes of illustration only, and are not intended to be limiting unless otherwise specified. Thus, the invention should in no way be construed as being limited to the following Examples, but rather, should be construed to encompass any and all variations which become evident as a result of the teaching provided herein.

EXAMPLES

Examples 1 through 5 recite working examples of formulations of anionic salicylate.

Example 1

Composition for anionic salicylate in solution

A 10% solution of anionic salicylate was prepared by dissolving 10 g of choline magnesium trisalicylate (Trilisate™, Purdue Frederick, Norwalk, Conn.) in 87 g of distilled water. The mixture was stirred until the choline magnesium trisalicylate was fully dissolved. Each gram of choline magnesium trisalicylate yielded 587 mg of choline salicylate, 725 mg of magnesium salicylate being equivalent to 1 gram of salicylate content. Final composition:

| anionic salicylate | 10% |
| choline and magnesium | 3% |
| water | 87% |

Example 2

Composition for anionic salicylate in lotion

A lotion was prepared by dissolving 4.9 g of magnesium salicylate (Doans™, Novartis, East Hanover, N.J.) in 30 ml of distilled water to produce a solution. The mixture was stirred until fully dissolved. The mixture was evaporated to form a slurry. 20.7 g of Jergens® lotion was added to the slurry to produce the following composition:

| anionic salicylate | 20% |
| moisturizing lotion | 80% |
| magnesium cation | 33.5 meq (0.3 g or 0.07%) |

Example 3

Composition for anionic salicylate in solution

A 5% solution of anionic salicylate was prepared by dissolving 5 g of magnesium salicylate (Doan™, Novartis, East Hanover, N.J.) in 95 g of isopropyl alcohol 70% (w/v) to yield the following composition:

| anionic salicylate | 5% |
| isopropyl alcohol | 66.5% |
| water | 28.5% |

A practitioner skilled in this art would readily recognize that other solubilizing agents could be employed depending on cosmetic or aesthetic considerations.

Example 4

Composition for anionic salicylate in lotion using salicylsalicylic acid

A lotion containing anionic salicylate was prepared by dissolving 10 g of salicylsalicylic acid (Salflex™, Carnrick, Cedar Knolls, N.J.) in 40 ml of carbonated water. The mixture was stirred until the salicylsalicylic acid was fully dissolved and allowed to evaporate to a slurry. 90 g of Jergens® (Kao Kabushiki Kaisha, Ltd., Tokyo, Japan) lotion were added to the slurry with stirring until there was a smooth consistency for the mixture, to produce the following composition:

| anionic salicylate | 10% |
| moisturizing lotion | 90% |

Example 5

Composition for anionic salicylate in cream

A cream containing anionic salicylate was prepared by dissolving 4.9 g of magnesium salicylate (Doans®, Ciba-Geigy Corp., Tarrytown, N.Y.) in 30 ml of distilled water. The mixture was stirred and allowed to evaporate to a slurry. The slurry was added to and mixed thoroughly with 41.4 g of Jergens® cream to produce the following composition:

| anionic salicylate | 10% |
| moisturizing cream | 90% |
| magnesium cation | 33.5 meq (0.3 g or 0.07%) |

Example 6

Composition for anionic salicylate in facial wash

A facial wash containing anionic salicylate was prepared by dissolving 4.9 g of magnesium salicylate (Doans®) in 30 ml of distilled water. The mixture was stirred and allowed to evaporate to a slurry. The slurry was added to and mixed thoroughly with 41.4 g of Almay® (Revlon Consumer Products Corp., New York, N.Y.) facial cleansing cream to produce the following composition:

| anionic salicylate | 10% |
| moisturizing lotion | 90% |
| magnesium cation | 33.5 meq (0.3 g or 0.07%) |

The following examples demonstrate the therapeutic efficacy of anionic salicylate for treating skin disorders according to the present invention.

Example 7

Treatment of acne with 20% topical anionic salicylate

A 47-year old male suffering from nodulocystic acne since adolescence had undergone several therapies. Benzoyl peroxide was never effective, tretinoin was helpful but was abandoned due to severe irritation and photosensitivity. Oral tetracycline was needed on almost a continuous basis resulting in good results when actively used but severe relapses occurred shortly after discontinuation. A topical anionic salicylate composition prepared from magnesium choline trisalicylate as a 20% composition in an aqueous 30% solution of isopropyl alcohol was applied to his face three times a day on an ongoing basis, which resulted in near complete resolution of the acne. Improvement was noted within one week. Treatment was continued with twice daily application and this regimen maintained the improved state. An occasional recurrence consisted of single pustular or nodular lesions which resolved readily with additional in situ applications of the compound. For troublesome lesions the anionic salicylate composition was applied as often as 5 times a day and in a strength as high as 50% anionic salicylate. Facial oil production was markedly decreased, both visibly and palpably. Comedone formation was also markedly decreased. Discontinuing the treatment on two separate occasions resulted in prompt relapse with recurrence of all grades of acne lesions. No adverse effects, in particular, no drying, irritation or phototoxicity were experienced. To the contrary, sun exposure was well tolerated and he tanned in situations where he previously burned. After six months of treatment, the composition was replaced by a 10% lotion, then cream, with total remission of the acne which has been maintained for nine months.

Example 8

Treatment of acne with 10% aqueous choline and anionic salicylate

A 15-year old female had the typical papular/pustular lesions of acne primarily on her forehead and at times on other areas of her face, as well. A composition made using the composition of Example 1, containing 10% anionic salicylate, was applied to the affected area twice daily for 2 weeks. The lesions dried over 1 to 2 days with full resolution within 7 days. She continued to use the composition every few weeks for a few days at a time with good results. She reported a high degree of satisfaction compared to other treatments and was particularly impressed with the composition's ability to quickly remedy acute inflammatory lesions.

Example 9

Treatment of acne with 10% choline and anionic salicylate

A 13-year old female with mild comedo/papular facial acne who had never required medical attention had self-medicated herself with over the counter preparations containing either benzoyl peroxide or 2% salicylic acid. She used a composition made, using the composition of Example 1, containing 10% anionic salicylate, every few weeks for a few days at a time. Good results were obtained. She rated this treatment an equally effective alternative to the treatments used in the past.

Example 10

Treatment of seborrheic dermatitis with 20% anionic salicylate

A 44-year old female suffering from seborrheic dermatitis of the scalp was not responsive to commercial anti-seborrheic shampoos alone. She obtained good relief from topical 0.1% triamcinolone cream, a topical steroid, and used this for a number of years. A 20% solution of anionic salicylate, made following the procedure of Example 1, but with twice the amount of choline magnesium trisalicylate and 10 ml less water, was prepared. This composition, applied twice daily for 2 weeks, was substituted with efficacy equal to that of the topical steroid. She continued to use it on an as-needed basis.

Example 11

Treatment of seborrhea with 10% anionic salicylate

A 28-year old female experienced excessive facial oiliness not associated with acne since adolescence. She had always found this very cosmetically unsightly and had used numerous proprietary preparations such as astringents and facial washes. She washed her face frequently, often 5–6 times a day, and carried astringent pads in her purse. Oil free makeup only provided temporary improvement in the appearance of her complexion and had to be removed and then reapplied throughout the day. She began using a 10% solution of anionic salicylate, made using a procedure similar to Example 1, with immediate noticeable improvement. Anionic salicylate eliminated the facial shine and uncomfortable sensation of greasiness for up to 12 hours at a time. Twice daily application completely resolved the problem. She discontinued frequent washing and use of astringents with an attendant improvement in her complexion. She noted her face to be less dry and softer to the touch. On days when the solution was not applied, the oily nature of her complexion returned. She reported no unpleasant side effects from the treatment.

Example 12

A 36-year old woman suffered from nodular acne of the face since adolescence. She had never sought medical attention. She used available over-the-counter acne treatments with modest efficacy. She rarely was without visible lesions and experienced pronounced exacerbations at the time of menstruation. Treatment was initiated with a cream of 10% anionic salicylate applied twice daily. Improvement was noted within one week, and by two weeks, she was lesion-free. Her face was noted to be much less oily. Examination after one month of treatment revealed her complexion to be completely clear of acne lesions and much less oily. She has continued treatment for three months with persistent therapeutic effect. Additionally, perimenstrual breakouts have completely ceased. She has suffered none of the side effects associated with prior treatments, e.g., dryness, redness and irritation. She rates the treatment as far superior to 10% benzoyl peroxide or 2% salicylic acid.

Example 13

A 49-year old woman sought treatment because of facial blemishes. She developed acne in her early 20s for which she was treated with retinoic acid and chemical peeling. Her acne gradually improved over the next 20 years but she continued to be dissatisfied with her complexion which remained oily. Her face was easily irritated and cosmetically bothersome blemishes were usually present. She began applying a cream containing anionic salicylate, first at a concentration of 5% for two months, with an increase to 10% thereafter. Her skin became blemish-free within a month and was less oily. Over six months, she has noted a progressive improvement in skin texture and color with no apparent side effects.

Example 14

The individual in Example 6 also suffered from acne involving his back. He applied a lotion of 10% anionic salicylate to the involved region once daily which resulted in drying of active lesions within 24–48 hours and complete resolution within 7 days. The fact that the involved area was covered, and therefore inconspicuous, allowed an alternating A-B-A treatment paradigm of two weeks of treatment followed by two weeks without treatment. Treatment consistently resulted in total eradication of acne lesions. Lesions consistently recurred in the untreated state. This on-off treatment paradigm was repeated for four full cycles demonstrating a direct cause and effect relationship between treatment with anionic salicylate and resolution of acne lesions.

Example 15

Reduction of sebum on the forehead treated with anionic salicylate

This Example was performed to compare treatments of the present invention using 10% and 50% anionic salicylate according to the present invention with 10% acetylsalicylic acid, 10% 5-aminosalicylic acid and 2% salicylic acid treatments and control conditions (no treatments) to determine the effect of the treatments or lack of treatments on sebum formed on the forehead.

The 47-year old male having a history as noted in Example 7, and after 9 months of such treatment, was tested for production and reduction of sebum on the forehead using 10% anionic salicylate, 10% acetylsalicylic acid, 10% 5-aminosalicylic acid, 50% anionic salicylate or 2% salicylic acid applied separately at different times. Active treatment was discontinued for 7 days before the first test was performed.

Figure 2:
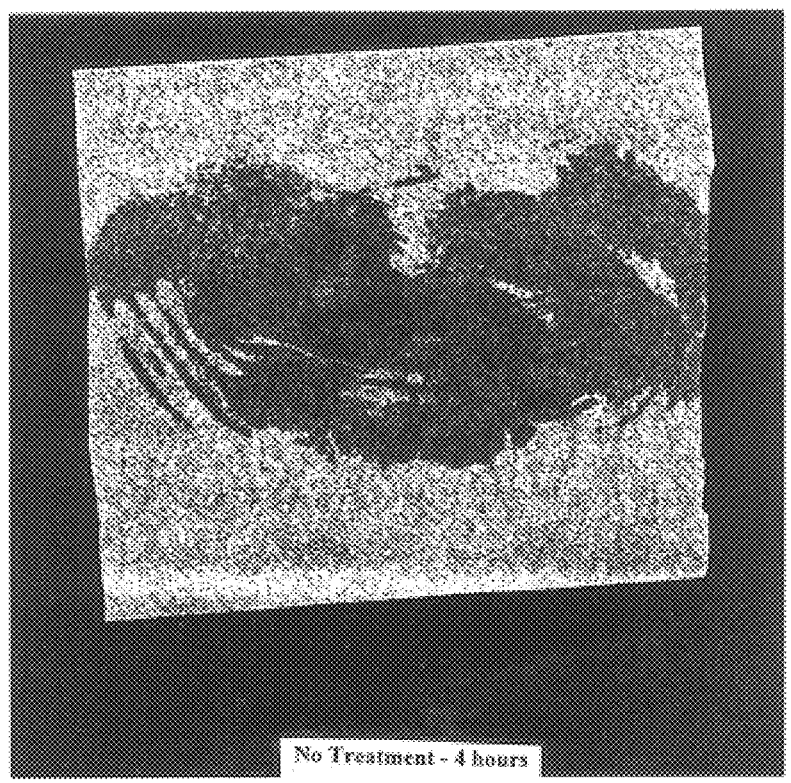
FIG. 2 is a photograph of a tissue paper blot of the forehead of same individual as in FIG. 1 without any treatment to the forehead 4 hours after cleansing with soap and water and drying, to establish a no-treatment control.

On the following morning at 8:00 A.M., the forehead was cleansed with soap and water and patted dry, but no treatments were applied. Immediately after cleansing, a baseline tissue paper blot was obtained by applying tissue paper to the forehead for 10 seconds with mild pressure, to obtain the baseline blot as shown in FIG. 1. Four hours after cleansing, a tissue paper blot of the forehead as shown in FIG. 2 was obtained by applying tissue paper for 10 seconds with mild pressure. This represents the control condition without any treatment.

A solution containing 10% anionic salicylate was prepared, following the procedure of Example 1. Other test compositions were prepared following similar procedures but using different amounts and types of active ingredients.

The procedure for testing the various compositions for sebum reduction is as follows: Cleansing of the forehead occurred at 8:00 A.M. The forehead, a conventional measurement site for sebum production, was cleansed with soap and water and the area was patted dry. Absorbent paper or absorbent tape are conventionally used to visualize sebum production.

Figure 3:
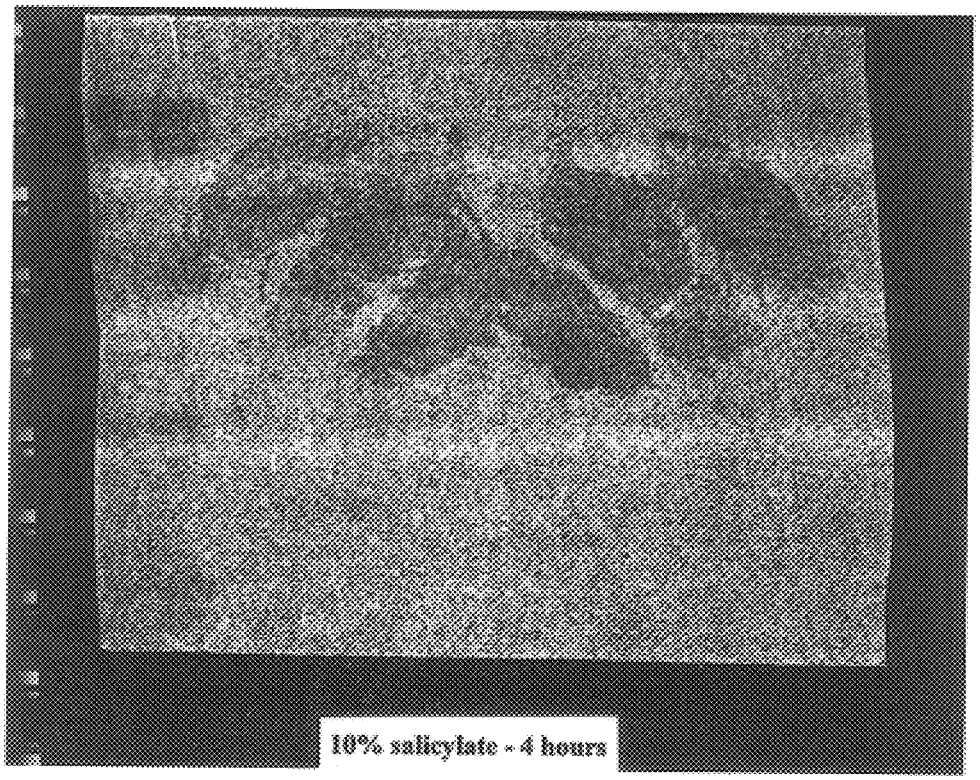
FIG. 3 is a photograph of a tissue paper blot of the forehead of same individual as in FIG. 1 at 4 hours after treatment with 10% anionic salicylate to the forehead according to the present invention.

The next day, after the forehead was patted dry, a solution of 10% anionic salicylate was applied to the forehead. After another 4 hours, tissue paper was applied to the forehead with mild pressure to the area for 10 seconds, resulting in the blot shown in FIG. 3. Treatment was then discontinued for seven days.

Figure 4:
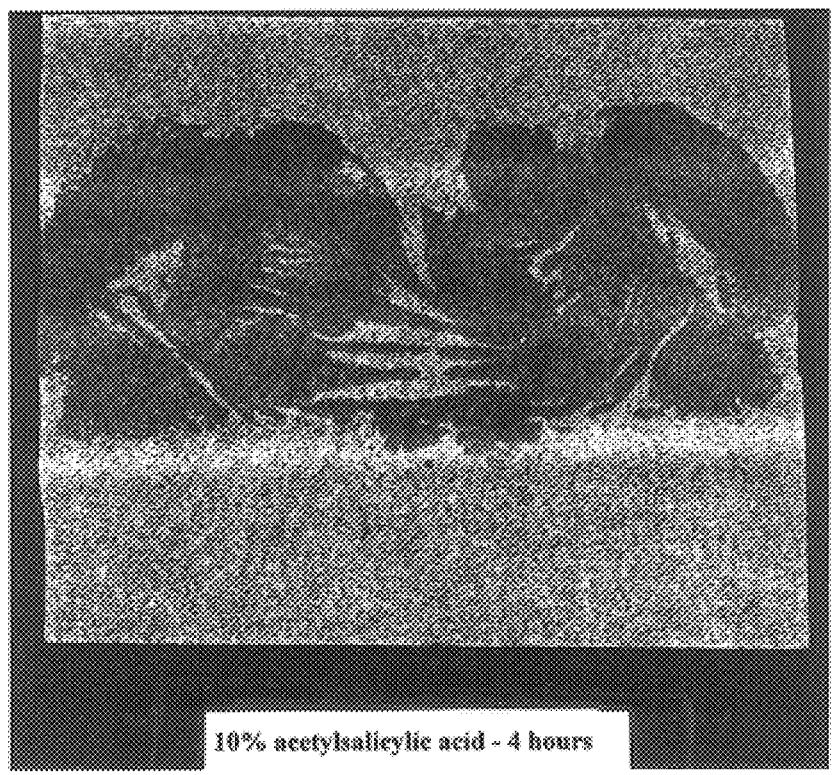
FIG. 4 is a photograph of a tissue paper blot of the forehead of same individual as in FIG. 1 at 4 hours after treatment with 10% acetylsalicylic acid to the forehead for comparison purposes with FIGS. 2 and 3.

On the following morning at 8:00 A.M., the forehead was cleansed again with soap and water. After the forehead was patted dry, a 10% solution of acetylsalicylic acid was applied to the forehead. Four hours after treatment with the 10% solution of acetylsalicylic acid, a tissue paper blot was obtained of the area as shown in FIG. 4 by applying tissue paper to the forehead for 10 seconds with mild pressure. After the test with 10% acetylsalicylic acid, the individual resumed using the 10% anionic salicylate for a few weeks. The individual again stopped all treatments for 7 days.

Figure 5:
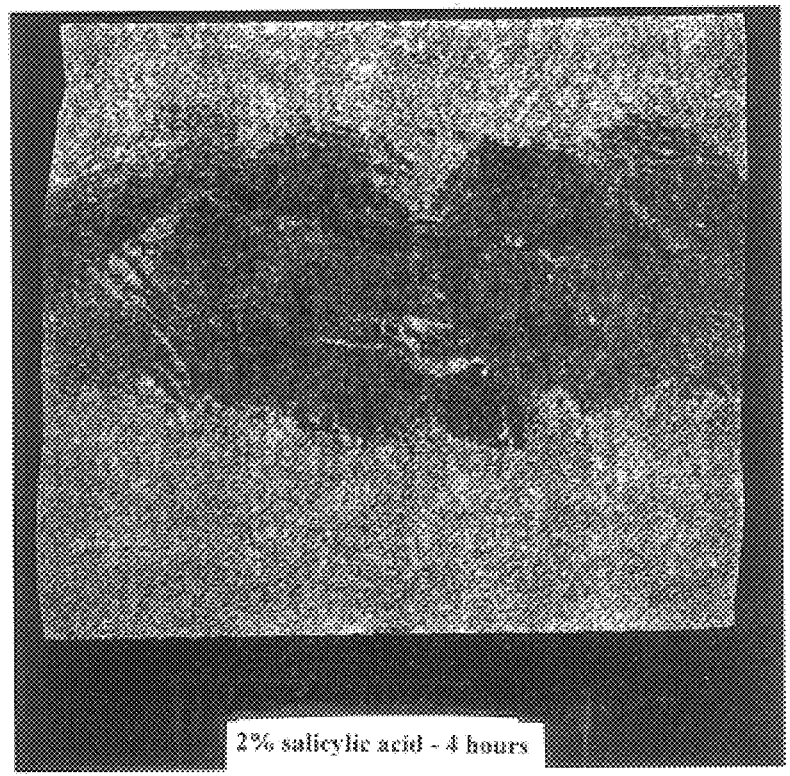
FIG. 5 is a photograph of a tissue paper blot of the forehead of same individual as in FIG. 1 at 4 hours after treatment with 2% salicylic acid to the forehead for comparison purposes with FIGS. 2 and 3.

At 8:00 A.M. the following day, the forehead was cleansed again with soap and water and the area was patted dry. A 2% solution of salicylic acid which was impregnated on a commercially available pad (Stri-Dex®, Blistex Inc., Oak Brook, Ill.) was applied to the forehead. Four hours after treatment, a tissue paper blot of the treated area as shown in FIG. 5 was obtained by applying tissue paper to the forehead for 10 seconds with mild pressure.

Figure 6:
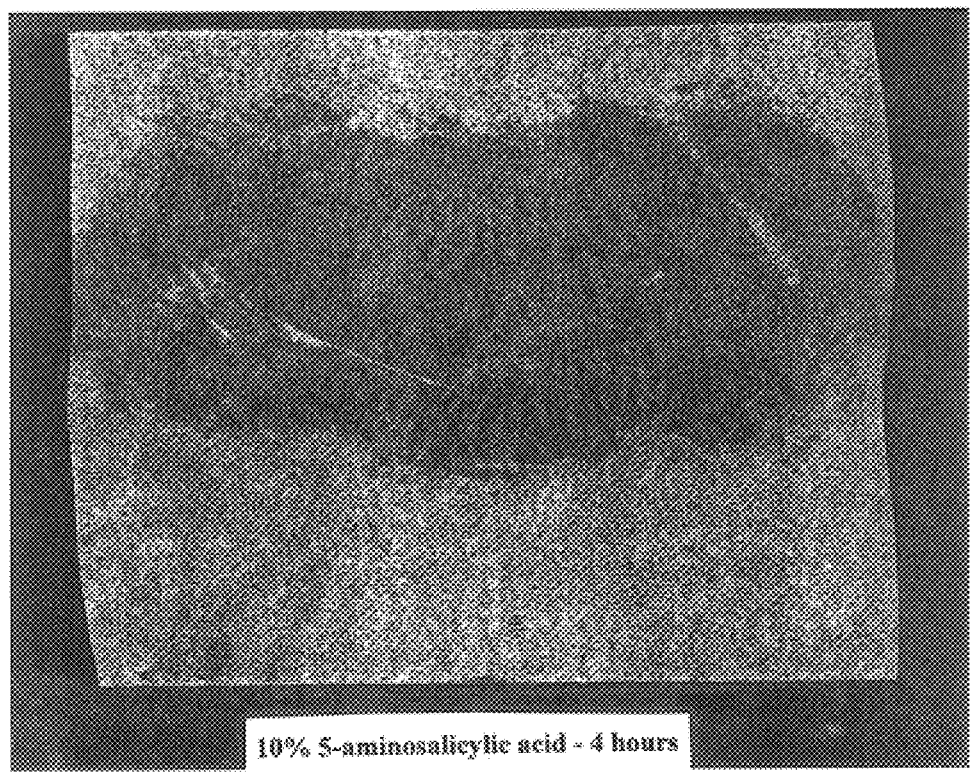
FIG. 6 is a photograph of a tissue paper blot of the forehead of same individual as in FIG. 1 at 4 hours after treatment with 10% 5-aminosalicylic acid to the forehead for comparison purposes with FIGS. 2 and 3.
Figure 7:
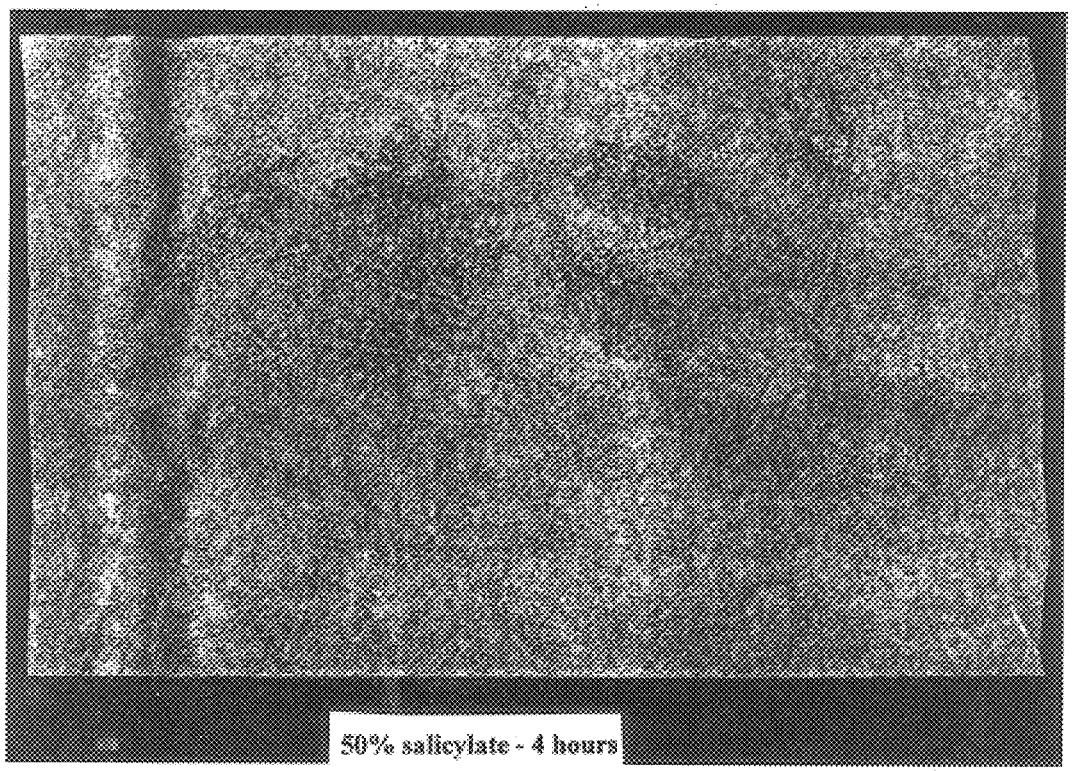
FIG. 7 is a photograph of a tissue paper blot of the forehead of same individual as in FIG. 1 at 4 hours after treatment with 50% anionic salicylate to the forehead according to the present invention.
Figure 8:
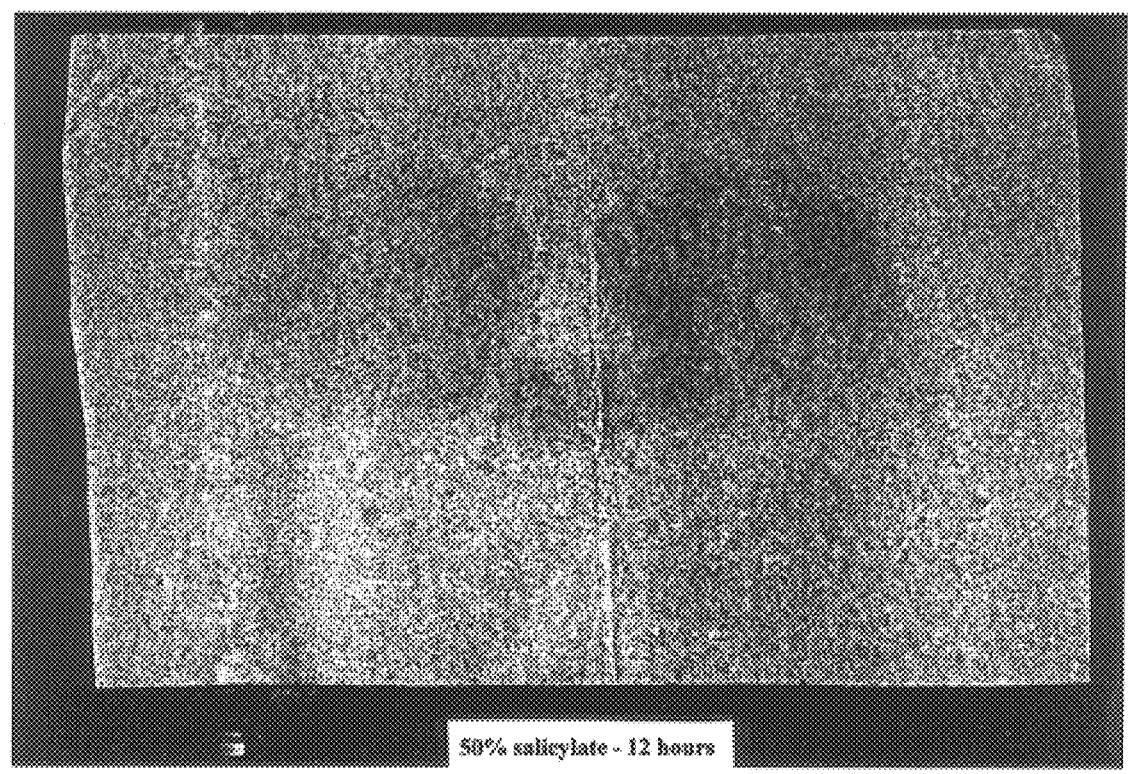
FIG. 8 is a photograph of a tissue paper blot of the forehead of same individual as in FIG. 1 at 12 hours after treatment with 50% anionic salicylate to the forehead according to the present invention.
Figure 9:
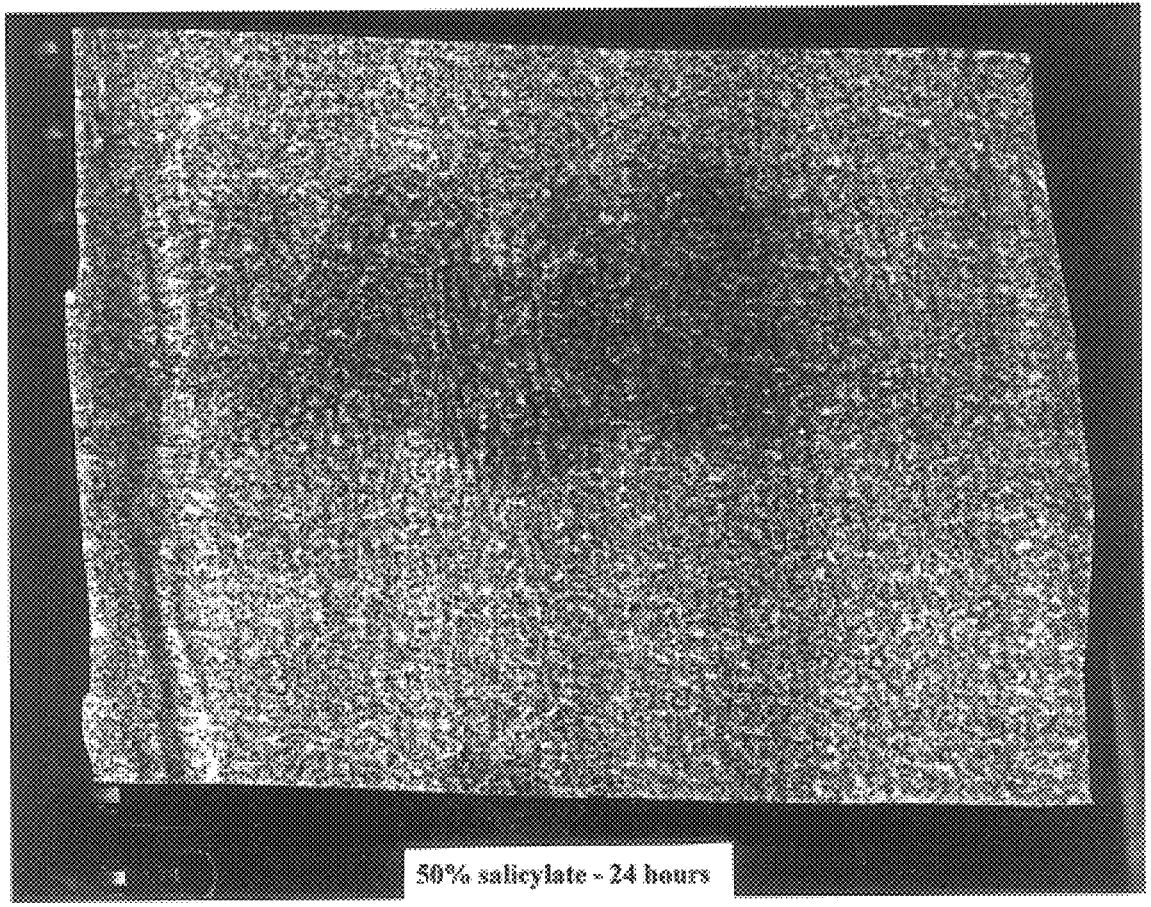
FIG. 9 is a photograph of a tissue paper blot of the forehead of same individual as in FIG. 1 at 24 hours after treatment with 50% anionic salicylate to the forehead according to the present invention.

The same procedure was followed for the tests with 10% 5-aminosalicylic acid and 50% anionic salicylate each after a seven day period of no treatments. The forehead was cleansed with soap and water, patted dry, and the 10% solution of 5-aminosalicylic acid was applied. A 4-hour blot was then obtained (FIG. 6). Maintenance treatment with 10% anionic salicylate was resumed. To test the possibility of a dose-effect relationship, 50% anionic salicylate was used as the test solution. Tissue paper blots were obtained at 4, 12 and 24 hours after application (FIGS. 7, 8 and 9, respectively).

A photocopy was made of each blot. Since sebum is opaque, light transmission varies with the amount of sebum present. The results of the treatments were compared to the baseline and the control, wherein the baseline is a tissue paper blot of the forehead of the same individual immediately after cleansing with soap and water (FIG. 1) and the control is the tissue paper blot of the forehead of same individual without any treatment to the forehead 4 hours after the start of the test (FIG. 2). The tissue paper blots were compared by visually inspecting the density of the dark area representing the absorption of sebum by the tissue paper. Greater sebum absorption, resulting from greater sebum production, produced a darker area and a larger area of darkness. The size and density of the blots after treatment with anionic salicylate were markedly reduced. The density was much less and the size of the blots was much smaller for the treatments with anionic salicylate after 4 hours (FIG. 3) in contrast to the tissue paper blot of the forehead treated with 10% acetylsalicylic acid (FIG. 4), the tissue paper blot of the forehead treated with 2% salicylic acid (FIG. 5) and the tissue paper blot of the forehead treated with 10% 5-aminosalicylic acid (FIG. 6), which have greater density of dark areas and larger sizes. The application of anionic salicylate on the forehead (FIG. 3) effectively reduced the presence of sebum, compared to no treatment (FIG. 2) and to the treatment with the 10% acetylsalicylic acid (FIG. 4), 2% salicylic acid (FIG. 5) and 10% 5-aminosalicylic acid (FIG. 6). FIG. 7 (50% anionic salicylate) demonstrates nearly complete suppression of sebum production at 4 hours, with persistence but with some gradual diminution of this effect at 12 and 24 hours (FIGS. 8 and 9, respectively). The results of these studies demonstrate the effectiveness of the treatment of the present invention in controlling sebum compared to the control blot or to any other treatments. Visual inspection demonstrates no effect on sebum production of 10% acetylsalicylic acid (FIG. 4), 2% salicylic acid (FIG. 5) or 10% 5-aminosalicylic acid (FIG. 6) when compared to the control blot (FIG. 2).

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

What is claimed is:

1. A method of treating or maintaining remission of a skin disorder caused totally or in part by the excessive production of sebum with a topical composition whereby the topical composition contains anionic salicylate or a precursor compound able to ionize anionic salicylate applied to areas of human skin that excrete excessive amounts of sebum wherein such composition is able to decrease sebum production and thereby, beneficially affect the disorder in question.

2. The method of claim 1 where the composition contains anionic salicylate or a precursor compound able to ionize to anionic salicylate.

3. The method of claim 1 where the precursor compound of anionic salicylate is freely soluble in water as defined by a log octanol/water partition coefficient of less than 1.

4. The method of claim 1 where the precursor compound of anionic salicylate freely dissociates in water as defined by a solubility product constant ($K_{sp}$) where the exponent is positive and the degree of ionization is complete or nearly complete.

5. The method of claim 1 where the precursor compound is a salt of salicylic acid.

6. The method of claim 1 where the precursor compound salt of salicylic acid is preferably chosen from the group consisting of magnesium salicylate, choline salicylate, choline magnesium trisalicylate, sodium salicylate, zinc salicylate, manganese salicylate or copper salicylate.

7. The method of claim 1 where the skin disorder is acne.

8. The method of claim 1 where the skin disorder is seborrhea.

9. The method of claim 1 where the skin disorder is seborrhea sicca.

10. The method of claim 1 where the skin disorder is seborrheic dermatitis.

11. A method of treating or maintaining remission of a skin disorder caused totally or in part by the excessive proliferation of keratinocytes with a topical composition whereby the topical composition contains anionic salicylate or a precursor compound able to ionize anionic salicylate applied to areas of human skin where excessive keratinocyte proliferation occurs wherein the composition is able to decrease the proliferation of keratinocytes.

12. The method of claim 1 where the composition contains anionic salicylate or a precursor compound able to ionize to anionic salicylate.

13. The method of claim 1 where the precursor compound of anionic salicylate is freely soluble in water as defined by a log octanol/water partition coefficient of less than 1.

14. The method of claim 1 where the precursor compound of anionic salicylate freely dissociates in water as defined by a solubility product constant ($K_{sp}$) where the exponent is positive and ionization is complete or nearly complete.

15. The method of claim 1 where the precursor compound is a salt of salicylic acid.

16. The method of claim 1 where the precursor compound salt of salicylic acid is preferably chosen from the group consisting of magnesium salicylate, choline salicylate, choline magnesium trisalicylate, sodium salicylate, zinc salicylate, manganese salicylate or copper salicylate.

17. The method of claim 9 where the skin disorder is acne.

18. The method of claim 9 where the skin disorder is psoriasis.

19. The method of claim 9 where the skin disorder is eczema.

* * * * *